United States Patent [19]

Clements

[11] Patent Number: 4,826,821

[45] Date of Patent: May 2, 1989

[54] LUNG SURFACTANT COMPOSITIONS

[75] Inventor: John A. Clements, Tiburon, Calif.

[73] Assignee: The Regents of the University of California, Berkeley, Calif.

[21] Appl. No.: 927,340

[22] Filed: Nov. 5, 1986

Related U.S. Application Data

[63] Continuation of Ser. No. 749,122, Jun. 26, 1985, abandoned, which is a continuation of Ser. No. 542,453, Oct. 17, 1983, abandoned.

[51] Int. Cl.$^4$ ............................................. A61K 31/685
[52] U.S. Cl. ..................................................... 514/78
[58] Field of Search ........................................... 514/78

[56] References Cited

U.S. PATENT DOCUMENTS 4,312,860  1/1982  Clements .............................. 424/199

OTHER PUBLICATIONS

Chemical Abstracts, vol. 86 (1977), #66212c; Soler-Argilaga et al.
Chemical Abstracts, vol. 85 (1976), #187244c; Melin et al.
Science, vol. 111 (1950), pp. 688 and 689, Glassman.

*Primary Examiner*—Leonard Schenkman
*Assistant Examiner*—Joseph A. Lipovsky
*Attorney, Agent, or Firm*—Phillips, Moore, Lempio & Finley

[57] ABSTRACT

An improved synthetic lung surfactant consists essentially of dipalmitoyl phosphatidyl choline, a C-14 to C-18 fatty alcohol (preferably hexadecanol), and a nontoxic nonionic surface active agent (preferably tyloxapol). The surfactant is prepared in a powdered lyophilized form that can be stored for extended periods at room temperature. The powdered product can be readily reconstituted by simply adding distilled water.

7 Claims, No Drawings

LUNG SURFACTANT COMPOSITIONS

This is a continuation of Ser. No. 749,122, filed June 26, 1985, now abandoned, which is a continuation of Ser. No. 542,453, filed Oct. 17, 1983, now abandoned.

BACKGROUND OF THE INVENTION

The present invention is directed to compositions useful in alleviating the symptons of mammalian respiratory distress syndrome (RDS). Such distress syndrome may occur in newborn infants, and especially in those born prematurely; or, in some instances it may occur in mature individuals when disease or trauma causes lung failure characterized by deficiency of lung surfactant. When such syndrome occurs, medical intervention may be initiated to aid the victim over the critical period until the body's natural surfactant mechanism can develop or revive to supply the lungs with the naturally occurring surfactant. In the interim, the compositions of this invention may be introduced into the lungs of the distressed individual to temporarily provide the surfactant necessary for proper pulmonary function.

This invention was made with government support under grant No. HL 24075 awarded by the Department of Health and Human Services. The government has certain rights in this invention.

Respiratory distress syndrome occurs in newborn infants, especially in those who are born prematurely. RDS also occurs in older children and adults. The incidence in infants is currently about 30,000 a year and in older patients about 100,000 a year in the United Stated of America alone. The per capita rate is about the same in other countries. The syndrome is manifest by lung failure and the concurrent deficiency of lung surfactant. It is the commonest cause of death in the newborn and is an important contributor of mortality in adult intensive care units.

In the past several decades a number of investigators have investigated and written of the physiology of the mammalian lung. These studies have elucidated the mechanisms involved in the transfer of gases from the airspaces in the lungs across the lining tissues to the underlying vascular system. These studies have revealed the critical role played by a liquid film which lines the lung tissue surfaces. This liquid film incorporates "surfactant" therein to facilitate the proper operation of the mammalian lung. Specifically the system operates on basic physical principles involving surface tension. That is the mechanism operates through the utilization of liquid surfaces incorporating particular molecular structures dissolved therein which result in a "skin-like" effect. This phenomenon underlies the tendency of the lung's airsacs or alveoli to expel gas at all times during the respiratory cycle. If sufficiently low surface tension forces are not maintained at the lung-tissue interface, the alveoli collapse during exhalation. Even the inspiration of air through the bronchi may be ineffective in inflating collapsed alveoli. Thus gas exchange in the pulmonary circulatory system may be inadequate in the absence of the required specialized liquid surfaces.

Establishing and maintaining low surface tension at the alveolar surfaces is accomplished by an intricate biological system associated with alveolar lung tissue. Special cells commonly known as alveolar Type II cells synthesize a complex mixture of lipids, proteins, glycerides and fatty acids. This complex molecular mixture is stored in the form of lamellar bodies within the alveolar Type II cells. By a mechanism little understood, the lamellar bodies are extruded from the alveolar Type II cells into alveolar lumen where the lamellae unwind and distribute the lipid, protein, glyceride and fatty acid molecules throughout the liquid film which bathes the entire cellular covering of the alveoli walls. These molecules are referred to by the medical community as "lung surfactant". When introduced to the alveolar surfaces and the liquid film thereon, they produce an essentially mono-molecular, all pervasive layer. The surfactant molecules effectively lower the surface tension of the film to values of 10 millinewtons/meter or less which is sufficient to maintain alveolar inflation during all phases of the respiratory cycle.

The composition of lung surfactants has been investigated and the results published in a number of papers such as Respiratory Distress Syndrome, Academic Press Inc., 1973, pages 77–98. These investigations indicate that natural lung surfactant is a complex mixture of many components, the major component of which is a lipid, dipalmitoyl phosphatidyl choline (1,2 dipalmitoyl-sn-3-glycerophosphoryl choline). Dipalmitoyl phosphatidyl choline commonly abbreviated as DPPC, occurs in lung surfactant to the extent of about 41% by weight. Mixed lecithins make up about 25% by weight; cholesterol makes up about 9 % by weight; mixed proteins about 9% by weight; phosphatidyl ethanolamine, about 5%; various glycerides and phosphatidyl serine and phosphatidyl glycerol, about 4%, respectively; lysolecithin, about 2%; with sphingomyelin and fatty acids, each making up about 1%. The above noted materials and percentages are for surfactant removed from canine lungs; however the mix of materials and percentages generally hold true for the higher mammals. Both bovine and human lung surfactant also comprise a similar mix, with DPPC running in the same range of approximately 40% by weight.

Respiratory distress syndrome occurs when the necessary surfactant is either absent from, or seriously depleted in, the liquid lining of the alveolar spaces. This syndrome occurs frequently in the newborn; and especially in the premature newborn. In such individuals development of the alviolar Type II cells has not yet arrived at a stage sufficient to generate the necessary surfactant material. The maturation of the alverolar Type II cells normally occurs within the last several weeks of full term gestation. In some instances, however, congenital defects interfere with and/or delay maturation of alveolar Type II cells; or more commonly in the instance of premature birth, maturation has not progressed sufficiently to generate the necessary surfactant.

In other instances, interruption of the generation of surfactants may occur in the mature and/or adult individual under the impact of disease and/or trauma.

It will be apparent from what has been noted hereinbefore that lack of the surfactant brought about either by immaturity, disease, or trauma interferes with the ability of the lung to properly inflate during the respiration process. The absence or loss of lung surfactant can result in the collapse or deflation of the alveolar spaces thereby resulting in severe respiratory distress. Such distress, if not managed by medical intervention, may most usually result in death. In the past such medical intervention included measures such as supplying high levels of oxygen; positive pressure application to the lungs to provide adequate pulmonary ventilation; adequate attention to the maintenance of nutrition, fluid balance, blood volume, blood pressure etc. In addition, in the case of a premature newborn, it has been determined that introduction of corticosteroids induces rapid maturation of the natural surfactant production system. Steroid therapy, however, must be undertaken before the actual birth occurs in order to be truly effective in achieving early maturation of the surfactant producing systems. Where it is anticipated that a premature birth will occur, tests can be made for inadequate level of surfactant and steroid therapy can instituted to hasten the maturation of the natural surfactant production system. In many instances, however, premature birth is not anticipated and/or tests are not undertaken to note low levels of surfactants before birth.

Soon after birth the body's own corticosteroid system begins to function whereby the necessary corticosteroids are produced internally. If the infant can be maintained for relatively short periods of time, i.e. several days, maturation of the surfactant production systems will occur. Thus sufficient surfactant will soon be released into the alveolar surfaces to produce the low surface tension necessary for the full and unassisted expensive to maintain normal respiratory function.

In the case of mature individuals where the respiratory distress syndrome occurs because of disease and/or trauma, the body's natural repair mechanisms can be expected to begin functioning if the individual can be maintained for a few days. Hopefully the natural system will then be reactivated and take over the role of production of natural surfactant, to thus maintain a normal expansion of the alveolar spaces.

In order to maintain the distressed individual, over these relatively short periods of time, attempts have been made to replace the lacking surfactant with exogenous surfactant components. Such attempts were generally not successful until Fujiwara at al. (Lancet, January 12, 1980) used cow-lung extract fortified with DPPC and phosphatidyl glycerol, two of the principal components of natural lung surfactant. The Fujiwara et al. tests with such material were quite successful.

Some shortcomings of such a substitute surfactant derived from animal lung extracts are the undefined nature of the surfactant; the possibility of contamination with microorganisms; and especially the presence of foreign proteins which may lead to antigen sensitization in individuals to whom such extracts are administered. It is therefore desirable to develop a lung surfactant substitute whose composition is completely defined; wherein production may be controlled to essentially exclude any possibility of microbial contamination; and in which antigenic proteins are completely absent.

With regard to the preparation of artificial lung surfactant compositions which are free of protein, Metcalfe et al. reported (J. Applied Physiology Respiratory Environment Exercise Physiology 49, 1980) that a composition of 17 % DPPC, 20% egg phosphatidylcholine, 10% phosphatidyl inositol, and 1% palmitic acid exhibited acceptable properties. Similarly C.J. Morley at the 16th International Congress of Pediatrics held in Barcelona, Spain, September, 1980 reported that an artificial surfactant consisting of DPPC and unsaturated phosphatidyl glycerol showed promise.

The present inventor has shown in U.S. Pat. No. 4,312,860 issued Jan. 26, 1982 that a mixture of DPPC and a fatty alcohol, such as hexadecanol, effectively operates as a synthetic lung surfactant.

While the compositions referenced in the above-noted patent are useful lung surfactants and are acceptable from a medical standpoint, they do tend to aggregate and settle out during storage; and they must be carefully reconstituted if they have been stored in order to fully disperse the surfactant. It is necessary to resort to the use of organic solvents or sonication when the compositions are diluted immediately prior to use. The patented compositions should also be stored at low temperatures to prevent their deterioration before use. Thus it would be desirable to provide improved artificial lung surfactant compositions which can be easily stored and readily reconstituted for use. The present invention solves these problems.

BRIEF DESCRIPTION OF THE INVENTION

The present invention is broadly concerned with synthetic lung surfactant compositions which are composed of chemically pure molecular structures; which are easily prepared and easily administered; and which are made from components that are readily available from commercial sources. More specifically, the lung surfactant compositions consist essentially of three components, i.e., dipalmitoyl phosphatidyl choline (hereinafter DPPC), a fatty alcohol, preferably hexadecanol, and a physiologically acceptable surface active agent, especially nonionic polymers of the alkyl aryl polyether alcohol type.

DPPC constitutes the major component of the compositions, while the fatty alcohol and surfaceactive agent are minor constituents.

DPPC occurs naturally in mammalian tissues, being a lipid found in the cell contents. It also occurs as the major constituent in lung surfactant.

Fatty alcohols also occur naturally in biological systems. The fatty alcohol component of the lung surfactant may be any of a number of fatty alcohols having from 14–18 carbon atoms; and may be either saturated or unsaturated. The much preferred fatty alcohol is hexadecanol, or more specifically n-hexadecan-1-ol. Unsaturated alcohols, e.g. oleic alcohol may also be utilized. Other fatty alcohols may be used so long as they are physiologically acceptable, contribute to lowering the surface tension at the alveoli surfaces, and remain in the surface film for extended periods during the respiration process.

The third component in the synthetic lung surfactant compositions is a physiologically acceptable (non-toxic) surface active or dispersing agent that is compatible with both the DPPC and fatty alcohol. The surface active agent is preferably a nonionic polymeric reaction product of an aldehyde and an organic oxide. Such nonionic surface active agents as the polymeric alkyl aryl polyether alcohols are especially preferred. It is required that such agents have a very low, or negligible, toxicity to mammals. The addition of the surface active component to the invention compositions greatly enhances their stability and ease of administration to a distressed individual.

The particular advantages realized by the employment of the three noted components in synthetic lung surfactant compositions will be apparent from the following description.

It is therefore an object of the invention to provide improved synthetic lung surfactant compositions.

It is another object of the invention to provide synthetic lung surfactant compositions that are readily adsorbed onto the alveolar surfaces and lower the liquid surface tension thereon.

It is another object of the invention to provide improved synthetic lung surfactant compositions that may be prepared and stored as dry powders.

It is another object of the invention to provide improved synthetic lung surfactant compositions that may be prepared without sonication during initial preparation.

It is yet another object of the invention to provide improved synthetic lung surfactant compositions that may be reconstituted into the liquid state immediately prior to administration without the use of organic solvents or sonication.

DETAILED DESCRIPTION OF THE INVENTION

As noted above, the synthetic lung surfactant compositions of this invention are protein-free and consist essentially of three components.

The major component is dipalmitoyl phosphatidyl choline (DPPC), which is also the major component of naturally occurring lung surfactants. DPPC has been synthetized in the laboratory. It is a lipid, i.e. one of the broad class of organic compounds found in cells which are extractable by non-polar solvents such as chloroform, ether, and benzene. It is comprised of two palmitoyl moieties linked to a phospho-glyceride moiety, i.e., phosphatidyl choline. The structural formula may be depicted as:

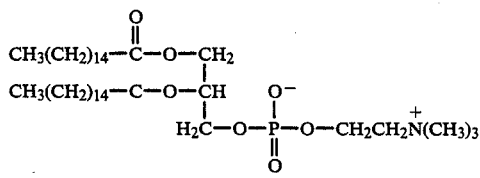

The lipid may be obtained in high purity on the commercial market.

DPPC is an essential component of the synthetic lung surfactant compositions and accounts for some of the desired properties of lung surfactant, i.e., it forms very stable monolayers at 37° C. and is a principal component of natural lung surfactant. DPPC may be present in the synthetic compositions over a fairly wide range, although in any event it constitutes the major component. Percentages in the low 80's or as high as the mid-90's relative to the the total weight of the DPPC and fatty alcohol (the lipids) are acceptable. Normally DPPC is present in about 90% by weight relative to the total weight of the DPPC and fatty alcohol. The remaining 10% of the lipid being fatty alcohol.

Alternatively, percentages of DPPC in the high 70's or as high as the mid-90's relative to the sum of the weights of the components of the DPPC, fatty alcohol, and surface active agent are acceptable. Normally, DPPC is present in about 90% by weight relative to the weight of the lipids.

the second component of the synthetic surfactant compositions is a fatty alcohol having carbons in the range of about 14–18. Such fatty alcohols may be either saturated or unsaturated, although the saturated alcohol, hexadecanol, is greatly preferred. The unsaturated alcohol, oleic alcohol, has also been utilized in experimental compositions and the resultant surfactants appear to have the desired properties. Any of the closely related fatty alcohols in the C-14 to C-18 range can also be utilized so long as the resultant surfactant composition satisfies the required properties of a lung surfactant. The fatty alcohols are available in high purity on the commercial market.

Alternatively, the fatty alcohol is present relative the sum of the components of DPPC, fatty alcohol and surface active agent in between about 7 and 10% by weight. Preferably it is between about 9 and 10% by weight of the total formulation as is described in the Examples below.

The alcohol component constitutes a minor percentage of the surfactant compositions, being present in an amount ranging from about 5% to about 20% by weight relative to the the total weight of the DPPC and fatty alcohol. Generally speaking the fatty alcohol is present in about 10% by weight relative to the total weight of the DPPC and fatty alcohol. The fatty alcohol may be present anywhere within the ranges noted above without unduly interfering with the properties of the lung surfactant.

The third component of the lung surfactant compositions comprises a physiologically acceptable surface active agent which, when mixed with the DPPC and fatty alcohol enhances a number of desired properties (storability, reconstitutability) of the synthetic lung surfactant. More specifically the third component comprises a non-toxic, nonionic dispersing agent preferably of the alkyl/aryl/polyether alcohol type. Such materials have the general structure:

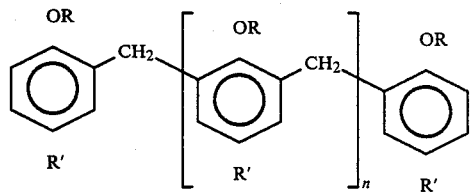

where
R = —CH$_2$CH$_2$O(CH$_2$CH$_2$O)$_m$CH$_2$CH$_2$OH
R' = —C(CH$_3$)$_2$CH$_2$C(CH$_3$)$_2$CH$_3$ and
m = 6 to 8; and
n = 4 or 5.

These surface active agents occur as a viscous liquid having a slight aromatic odor. The dispersing agent is slowly but freely miscible with water. Such materials also have an extremely low toxicity in the mammalian body.

The preferred surface active agent is a readily available material, commonly referred to as tyloxapol. It can be purchased under several trade names from various companies such as Sterling-Winthrop, and Rohm and Haas.

The extremely low toxicity of these surface active agents has been noted in the article by H.N. Glassman appearing in Science, Vol. 3, June 23, 1950, pages 688–689. Triton A-20, referred to in the Glassman article, is tyloxapol, the preferred surface active agent for use in the synthetic lung surfactant compositions.

The surface active agent is present in the lung surfactant compositions as a relatively small percentage by weight e.g. 6 to 11% of the total weight of the organic components of the formulation as is found in the examples. Its presence in the surfactant composition slows aggregation and settling of the lipid components; and enhances the rate of adsorption to the surface and enhances the speed of lowering surface tension. It permits self-assembly of the component directly from the powdered state into saline without the use of organic solvents or sonication; and facilitates reconstitution of the surfactant composition from lyophilized surfactant by the simple addition of distilled water immediately before use.

The synthetic lung surfactant compositions may be prepared by admixing both the DPPC and fatty alcohol (which are purchased as dry powders) with the dispersing agent that has been previously dissolved in saline. When thoroughly mixed, a uniform milky suspension results. If the resultant lung surfactant composition is to be stored for any period of time the milky suspension is lyophilized to produce a dry powdered material. If maintained in a sterile environment, the dry powder may be stored for extended periods of time. It is easily reconstituted with distilled water immediately prior to use.

The following example sets forth a typical preparation of lung surfactant compositions:

EXAMPLE I

Tyloxapol was secured from the SterlingWinthrop company. A tyloxapol-saline solution was first prepared by dissolving 250 milligrams of the tyloxapol in 0.1N sodium chloride solution to produce a total volume of 250 milliliters. solution. 810 milligrams of DPPC purchased from the Sigma Company and checked for purity (>98%) by chromatography, and 90 milligrams of hexadecanol purchased from Nu Chek Prep Company and checked for purity (>99%) by chromatography were placed as powders in a 25 by 200 mm screw cap tube. 60 mls of the tyloxapol-saline solution were added to the powdered materials. The tube was then tightly capped and rotated end-over-end for two hours in a 60° C. waterbath. A uniform milky suspension resulted; which was then aliquoted into lyophilization vials in 8 ml portions. The aliquots were then immediately frozen at −70° C. Water was then removed from the aliquots by lyophilization to a final pressure of 10 microns of mercury over a period of 24–30 hours. The vials were sealed while under a vacuum. The lyophilized powdery product was then stored at room temperature. For long storage periods the lyophilized powdered product can be stored at 4° C.

As noted in the above example the lyophilized powdered product can be stored for extended periods of time; however, since it is in the powdered form it must be reconstituted before use. The following example illustrates the manner in which the lyophilized powdered surfactant can be reconstituted and utilized in treating a patient suffering from RDS:

EXAMPLE II

One of the stored vials containing lyophilized lung surfactant as prepared according to Example I was selected. 8 ml of distilled water was drawn into a syringe with a 20 gauge hypodermic needle thereon. The vial cap was penetrated with the needle so that the water was drawn from the hypodermic needle under vacuum into the vial. When the water was introduced into the vial, the powdered lung surfactant spontaneously dispersed into the liquid. A second needle was then introduced to break the vacuum and the contents of the vial were then aspirated into the syringe. The reconstituted lung surfactant was then instilled into the lungs via an endotracheal tube. A dosage of 75 mg/kg (5 ml/kg) of body weight was sufficient to achieve the desired results.

Testing

As noted hereinbefore, besides being physiologically acceptable, the synthetic lung surfactant must adsorb quickly in the liquid surface bathing the alvioli; and it must form a stable film that lowers surface tension to very low values (10 milliNewtons/meter or less). A relatively simple in vitro test has been devised confirming the above-noted properties. This test is a "shake test" modified from a procedure devised by the inventor for the purpose of testing for natural surfactant in amniotic fluid. This test was originally disclosed in the New England Journal of Medicine, 286, pages 1077–1081, 1972.

The test is as follows:

A carefully mixed sample of synthetic lung surfactant composition and containing about 400 micrograms (about 25 microliters) surfactant composition is placed in a 20 ml culture tube. 2 ml of saline is then added and the tube is tightly capped. The tube is then immersed in a water bath held at 37° C. for a time (5 minutes) sufficient to equilibrate the temperature of the sample with that of the bath. The tube is then shaken vigorously by hand for 15 seconds and placed back into the bath to settle. The presence of copious foam at the meniscus indicates that the lung surfactant has been adsorbed into the saline and has created a film thereon. If the bubbles are tiny and remain for 15 minutes or more the test confirms that the surface film is stable and maintains a low surface tension.

All samples prepared according to the invention compositions passed the "shake test". Although the test is quite simple it has been shown to correctly assay the desired properties required by lung surfactant compositions.

In further testing, synthetic lung surfactant was prepared having the following composition:

EXAMPLE III DPPC (greater than 98% pure, Sigma Chemicals), 13.5 mg/ml, hexadecanol (greater than 99% pure, Nu Check Prep.) 1.5 mg/ml, surface active agent (Tyloxapol in 0.1 N NaCl, Sterling Winthrop). 1 mg/ml. DPPC and hexadecanol were dispersed by sonication into the surface active agent. The procedure was similar to that set forth in Example I.

The above noted composition formed a milky suspension that settled slowly in about an hour. It lowered aqueous surface tension rapidly, having a time constant of approximately 0.7 second. It produced a surface tension less than 10 millinewtons per meter on reduction of surface area. The surface films created by the above compositions were extremely stable having a foam test stability of greater than 8 days.

The synthetic lung surfactant composition, prepared according to Example III above, was also utilized in vivo tests.

In one test a group of rabbit fetuses were delivered very prematurely at 27 days of gestation. The synthetic lung surfactant composition was instilled into the rabbit fetus' lungs before breathing commenced, thereafter mechanical resuscitation was continued for 2 hours. In one group of rabbits only saline solution was instilled into the lungs; while in a second group the synthetic lung surfactant composition of Example III was instilled. In yet a third group, natural lung surfactant (isolated from adult animals) was instilled into the lungs. Table 1 below presents the results of the test.

TABLE 1

FETAL RABBIT LUNGS - PARAMETERS RELATED TO VENTILATORY MANAGEMENT

|  |  | Saline | SLS[1] | NLS[2] |
|---|---|---|---|---|
| Quasi-static P-V | P[4] opening 50% (FRC[3]) | 27 cm H$_2$O | 23 cm H$_2$O | 20 cm H$_2$O |
|  | P closing 40% (FRC) | 10 cm H$_2$O | 7 cm H$_2$O | 7 cm H$_2$O |
|  | P plateau | 20 cm H$_2$O | 20 cm H$_2$O | 20 cm H$_2$O |
| Conditioning-time to 60 ml/kg at 25 cm H$_2$O |  | 35 min. | 15 min. | 5 min. |
| Adsorption kinetics: |  |  |  |  |
| Surface Tension at 0.5 sec. |  | 70 mN M$^{-1}$ | 60 mN M$^{-1}$ | 45 mN M$^{-1}$ |
| Calculated P opening at 0.5 sec. and r = 50 micrometers |  | 27 cm H$_2$O | 23 cm H$_2$O | 17 cm H$_2$O |

[1]SLS = synthetic lung surfactant
[2]NLS = natural lung surfactant
[3]FRC = functional residual lung volume
[4]P = pressure As will be noted from the data presented in Table 1, in most respects the synthetic lung surfactant was intermediate between saline and natural lung surfactant. However it appears to be about equal with natural lung surfactant in stabilizing the functional residual volume of the lungs. In the Table, the conditioning refers to expansion of the lungs at a constant pressure of 25 cm H$_2$O. It is a guide to the speed with which distensibility can be improved. With adsorption kinetics data it is possible to calculate the opening pressure to be expected in lungs with airspace radius of approximately 50 micrometers.

In another group of in vivo experiments 10 pairs (including seven pairs of twins) of lambs were delivered by Caesarian section at 130–132 days. The fetuses were paralyzed before ligation of the umbilical cord, intubated, catheterized and resuscitated. Before mechanical ventilation was started one of each pair received 75 milligrams/kg of the synthetic lung surfactant by endotracheal instillation (as per Example III) and the other nothing.

Thereafter respiratory and circulatory support was optimized for each animal according to current practice in the intensive care nursery. Arterial CO$_2$ was maintained near 40 torr as well as possible by adjusting inspiratory pressure and ventilator frequency (60 to 40 breaths per minute). Arterial oxygen was kept, if possible, in the 80 to 100 torr range (after the first half hour) by adjusting the inspired oxygen concentration. The experiment was continued for 11 hours.

Eight of the eleven synthetic lung surfactant treated lambs survived the 11-hour experiment. Only three of the ten control animals survived eleven hours, despite attempts to optimize support. None of the 20 experimental animals developed pneumothorax. Arterial CO$_2$ could be normalized fairly well in the synthetic lung surfactant treated animals; whereas the controls tended to be hypercapneic. Arterial oxygen could be maintained; alveolar-arterial oxygen gradient, and inspired oxygen could be lowered more readily in the synthetic lung surfactant treated enimals than in the controls.

On the average, the synthetic lung surfactant treated animals required less pressure to ventilate, had higher lung compliance, and had higher lung volumes than the controls. Their blood pressures were comparable. The control animals tended to have higher pulmonary arterial pressures, but both groups decreased towards the end of the experiment. Upon autopsy, the lungs of the synthetic lung surfactant animals were well aerated for the most part, but the controls showed extensive collapse.

In summary, the results of the in vivo experiments indicated that in both prematurely delivered rabbit and lamb fetuses, lung deficits can be compensated to an important degree by the synthetic lung surfactant compositions.

What is claimed:

1. An improved synthetic lung surfactant composition having improved dispersant properties in aqueous suspension, as compared to a lung surfactant composition consisting essentially of dipalmitoyl phosphatidyl choline and a fatty alcohol having from 14 to 18 carbon atoms, which improved surfactant consists essentially of:

(a) dipalmitoyl phosphatidyl choline, which is present in at least 80% by weight of the total weight of the dipalmitoyl phosphatidyl choline and fatty alcohol, (b) a fatty alcohol having from 14 to 18 carbon atoms, which is present relative to the sum of the weights of the components of dipalmitoyl phosphatidyl choline, fatty alcohol and surface active agent in between about 7 and 10% by weight, (c) a non-ionic physiologically acceptable non-toxic surface active agent of the alkyl aryl polyether alcohol type of the structure:

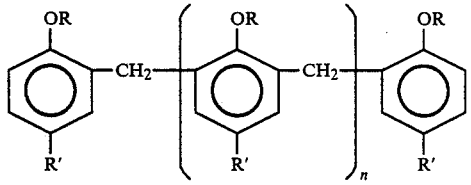

wherein
R=—CH$_2$CH$_2$O(CH$_2$CH$_2$O)$_m$CH$_2$CH$_2$OH;
R'=—C(CH$_3$)$_2$CH$_2$C(CH$_3$)$_2$CH$_3$;
m=6 to 8; and
n=4 or 5, which is present in about 6 to 11 percent by weight of the organic components of the composition; and (d) sodium chloride present as a minor component by weight.

2. The composition of claim 1 wherein the surface active agent is tyloxapol.

3. The composition of claim 2 wherein the dipalmitoyl phosphatidyl choline is at least 90 percent by weight of the total weight of the dipalmitoyl phosphatidyl choline and fatty alcohol.

4. The composition of claim 1 wherein is suspended in saline solution.

5. A powdered lyophilized lung surfactant composition, having improved dispersant properties in aqueous solution as compared to a lung surfactant composition consisting essentially of dipalmitoyl phosphatidyl choline and a fatty alcohol having from 14 to 18 carbon atoms, which improved surfactant composition consists essentially of dipalmitoyl phosphatidyl choline, a C-14 to C-18 fatty alcohol, a physiologically acceptable non-toxic non-ionic surface active agent of the alkyl aryl polyether alcohol type of the structure:

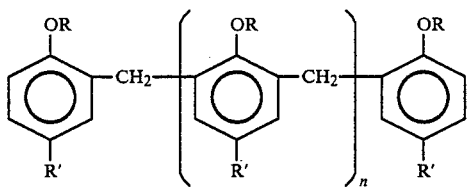

wherein
R=—CH₂CH₂O(CH₂CH₂O)ₘCH₂CH₂OH;
R'=—C(CH₃₂CH₂C(CH₃)₂CH₃;
m=6 to 8; and
n=4 or 5; and sodium chloride
wherein the dipalmitoyl phosphatidyl choline is present in at least 80 percent by weight of the total weight of the dipalmitoyl phosphatidyl choline and fatty alcohol, the fatty alcohol is present relative to the sum of the weights of the components of dipalmitoyl phosphatidyl choline, fatty alcohol and surface active agent in between about 9 and 10 percent by weight, the surface active agent is present in about 6 to 11 percent by weight of the sum of the organic components of the compositions, and sodium chloride is a minor component by weight.

6. The surfactant composition of claim 5 wherein the surface active agent is tyloxapol.

7. The compositin of claim 6 wherein the dipalmitoyl phosphatidyl choline is present in at least 90 percent by weight of the total weight of the dipalmitoyl phosphatidyl choline and fatty alcohol.

* * * * *